United States Patent [19]

Beaman

[11] Patent Number: 5,196,526
[45] Date of Patent: Mar. 23, 1993

[54] CDNA CLONE FOR T-CELL SUPPRESSOR INDUCER FACTOR

[75] Inventor: Kenneth D. Beaman, Gurnee, Ill.

[73] Assignee: University of Health Sciences/The Chicago Medical School, North Chicago, Ill.

[21] Appl. No.: 442,116

[22] Filed: Nov. 28, 1989

[51] Int. Cl.⁵ .................................... C07H 21/04
[52] U.S. Cl. ............................ 536/23.51; 530/350; 530/351; 530/399
[58] Field of Search ........................ 536/27, 28, 29

[56] References Cited

U.S. PATENT DOCUMENTS 4,713,332 12/1987 Mak ..................................... 435/70

OTHER PUBLICATIONS

Hoversland et al., *J. Reprod. Res.*, 88(1), 135-140 (1990).
Ward et al., *Nucleic Acids Research*, 15(17), 7195 (1987).
Bichko et al., *Fed Eur. Biochem. Soc. Lett.*, 185(1), 208-212 (1985).
Umesono et al., *J. Mol. Biol.*, 203, 299-331 (1988).
R. de Martin et al. "Complementary DNA for human gliobastomia-derived T cell suppressor factor, a novel member of the transforming growth factor-B gene family", The EMBO Journal vol. 6 No. 12 pp. 3673-3677, 1987.
Geoffrey L. Asherson et al. "An Overview of T-Suppressor Cell Circuits", Ann. Rev. Immunol. 1986 4:37-68.

*Primary Examiner*—Johnnie R. Brown
*Assistant Examiner*—L. Eric Crane
*Attorney, Agent, or Firm*—Wallenstein, Wagner & Hattis, Ltd.

[57] ABSTRACT

The invention generally discloses the cloning and characterization of a nucleotide sequence encode for at least a part of primate T-cell suppressor inducer factor (TsFl) protein and in particular, a putative gene for TsFl produced by the murine cell line A.1.1. The nucleotide sequence is 2936 bp in length comprising an encoding sequence 2565 bp in length and encoding a protein of 690 amino acids.

10 Claims, 7 Drawing Sheets

FIG. 1A

```
              MetGlySerLeuPheArgSerGluSerMetCysLeuAlaGln
GAGCGAGGCAGCGCCGCCATGGGCTCTCTCTTCCGCAGCGAGAGCATGTGCCTGGCGCAG
         10        20        30        40        50        60

LeuPheLeuGlnSerGlyThrAlaTyrGluCysLeuSerAlaLeuGlyGluLysGlyLeu
CTCTTCCTGCAGTCGGGCACGGCCTACGAGTGTCTGAGCGCGCTGGGCGAGAAGGGCCTG
         70        80        90       100       110       120

ValGlnPheArgAspLeuAsnGlnAsnValSerSerPheGlnArgLysPheValGlyGlu
GTGCAGTTCCGAGACCTCAATCAAAATGTAAGTTCTTTTCAAAGAAAATTCGTCGGTGAG
        130       140       150       160       170       180

ValLysArgCysGluGluLeuGluArgIleLeuValTyrLeuValGlnGluIleThrArg
GTAAAGAGGTGTGAAGAGCTCGAACGAATACTGGTGTACCTGGTGCAGGAAATCACCAGA
        190       200       210       220       230       240

AlaAspIleProLeuProGluGlyGluAlaSerProProAlaProProLeuLysHisVal
GCTGATATTCCCCTGCCTGAAGGAGAGGCCAGTCCTCCCGCACCACCTCTTAAACATGTC
        250       260       270       280       290       300

LeuGluMetGlnGluGlnLeuGlnLysLeuGluValGluLeuArgGluValThrLysAsn
CTAGAAATGCAGGAACAGCTGCAGAAGCTGGAGGTGGAGCTCAGAGAAGTCACCAAGAAC
        310       320       330       340       350       360

LysGluLysLeuArgLysAsnLeuLeuGluLeuValGluTyrThrHisMetLeuArgVal
AAGGAGAAGCTGAGGAAGAACCTGTTGGAGCTGGTGGAGTACACCCACATGCTGAGGGTC
        370       380       390       400       410       420

ThrLysThrPheLeuLysArgAsnValGluPheGluProThrTyrGluGluPheProAla
ACGAAGACCTTCCTCAAGCGGAATGTGGAGTTTGAGCCCACGTATGAAGAGTTTCCCGCC
        430       440       450       460       470       480

LeuGluAsnAspSerLeuLeuAspTyrSerCysMetGlnArgLeuGlyAlaLysLeuGly
TTAGAGAACGACTCTCTGTTGGACTACAGCTGCATGCAGCGGCTGGGCGCCAAGCTGGGA
        490       500       510       520       530       540

PheValSerGlyLeuIleGlnGlnGlyArgValGluAlaPheGluArgMetLeuTrpArg
TTCGTTTCTGGCCTGATTCAGCAAGGCAGAGTTGAAGCATTTGAAAGGATGCTGTGGCGG
        550       560       570       580       590       600

AlaCysLysGlyTyrThrIleValThrTyrAlaGluLeuAspGluCysLeuGluAspPro
GCCTGCAAAGGGTACACCATTGTGACCTATGCAGAGCTGGACGAGTGCCTGGAGGACCCT
        610       620       630       640       650       660

GluThrGlyGluValIleLysTrpTyrValPheLeuIleSerPheTrpGlyGluGlnIle
GAAACGGGTGAAGTCATAAAGTGGTACGTGTTCCTGATTTCCTTTTGGGGAGAGCAGATT
        670       680       690       700       710       720

GlyHisLysValLysLysIleCysAspCysTyrHisCysHisIleTyrProTyrProAsn
GGCCACAAGGTTAAGAAGATATGTGACTGTTACCACTGCCACATCTACCCGTATCCAAAC
        730       740       750       760       770       780
```

FIG. 1B

```
ThrAlaGluGluARgARgGluIleGlnGluGlyLeuAsnThrArgIleGlnAspLeuTyr
ACGGCTGAGGAGCGCAGGGAGATTCAGGAGGGGCTCAATACTCGGATCCAAGACCTTTAC
    790       800       810       820       830       840

ThrValLeuHisLysThrGluAspTyrLeuArgGlnValLeuCysLysAlaAlaGluSer
ACGGTGCTGCACAAAACGGAGGACTATCTGCGGCAAGTGCTCTGCAAAGCTGCCGAGTCC
    850       860       870       880       890       900

ValCysSerArgValValGlnValArgLysMetLysAlaIleTyrHisMetLeuAsnMet
GTGTGCAGCCGTGTGGTCCAGGTGAGGAAGATGAAGGCCATCTACCACATGCTCAACATG
    910       920       930       940       950       960

CysSerPheAspValThrAsnLysCysLeuIleAlaGluValTrpCysProGluValAsp
TGCAGCTTTGACGTCACCAACAAGTGCCTCATAGCTGAGGTCTGGTGCCCCGAGGTGGAC
    970       980       990       1000      1010      1020

LeuProGlyLeuArgArgAlaLeuGluGluGlySerArgGluSerGlyAlaThrIlePro
CTGCCAGGCTTGCGCAGAGCACTGGAGGAAGGCTCGAGAGAGAGCGGAGCTACAATCCCC
    1030      1040      1050      1060      1070      1080

SerPheMetAsnThrIleProThrLysGluThrProProThrLeuIleArgThrAsnLys
TCGTTCATGAACACAATCCCTACGAAAGAAACACCCCCCACTCTGATCCGCACCAACAAA
    1090      1100      1110      1120      1130      1140

PheThrGluGlyPheGlnAsnIleValAspAlaTyrGlyValGlySerTyrARgGluVal
TTCACTGAAGGTTTCCAGAACATCGTGGATGCCTATGGAGTCGGGAGCTACAGAGAAGTG
    1150      1160      1170      1180      1190      1200

AsnProAlaLeuPheThrIleIleThrPheProPheLeuPheAlaValMetPheGlyAsp
AACCCAGCTCTCTTTACCATCATCACCTTCCCGTTCCTGTTTGCTGTGATGTTTGGCGAC
    1210      1220      1230      1240      1250      1260

PheGlyHisGlyPheValMetPheLeuPheAlaLeuLeuLeuValLeuAsnGluAsnHis
TTTGGGCACGGCTTTGTCATGTTCCTGTTTGCCCTCTTACTGGTGTTAAATGAGAATCAC
    1270      1280      1290      1300      1310      1320

ProArgLeuSerGlnSerGlnGluIleLeuARgMetPhePheAspGlyArgTyrIleLeu
CCCAGACTAAGCCAGTCACAGGAGATCCTTAGGATGTTCTTTGACGGCCGGTATATCCTG
    1330      1340      1350      1360      1370      1380

LeuLeuMetGlyLeuPheSerValTyrThrGlyLeuIleTyrAsnAspCysPheSerLys
CTGCTGATGGGGCTGTTCTCTGTGTACACCGGCCTCATCTACAACGACTGCAAGAGGTTC
    1390      1400      1410      1420      1430      1440

SerValAsnLeuPheGlySerGlyTrpAsnValCysAlaMetTyrSerSerSerHisSer
TCTGTGAACCTCTTTGGTTCTGGGTGGAACGTATGTGCCATGTACAGCTCCAGCCACTCT
    1450      1460      1470      1480      1490      1500

ProGluGluGlnArgLysMetValLeuTrpAsnAspSerThrIleArgHisSerArgThr
CCAGAGGAGCAGAGGAAGATGGTACTTTGGAATGACAGCACCATCAGGCACAGCAGAACT
    1510      1520      1530      1540      1550      1560

LeuGlnLeuAspProAsnIleProGlyValPheArgGlyProTyrProPheGlyIleAsp
TTGCAGCTGGACCCGAATATCCCTGGAGTTTTCCGAGGCCCCTACCCTTTTGGCATTGAT
    1570      1580      1590      1600      1610      1620
```

F I G. 1C

```
ProIleTrpAsnLeuAlaThrAsnArgLeuThrPheLeuAsnSerPheLysMetLysMet
CCTATTTGGAACCTGGCCACAAACCGCCTCACGTTCCTCAACTCCTTCAAGATGAAAATG
       1630      1640      1650      1660      1670       1680

SerValIleLeuGlyIlePheHisMetThrPheGlyValValLeuGlyIlePheAsnHis
TCTGTGATTTTAGGAATTTTTCACATGACTTTTGGTGTTGTTCTGGGAATATTTAACCAC
       1690      1700       1710       1720      1730       1740

LeuHisPheArgLysLysPheAsnValTyrLeuValSerValProGluIleLeuPheMet
TTGCACTTTAGGAAGAAGTTCAACGTCTACCTGGTCTCGGTGCCTGAGATCCTGTTCATG
        1750      1760       1770      1780       1790      1800

LeuCysIlePheGlyTyrLeuIlePheMetIleIleTyrLysTrpLeuAlaTyrSerAla
CTCTGCATCTTTGGGTACCTGATTTTCATGATCATTTACAAGTGGCTGGCATACTCGGCA
       1810      1820      1830      1840      1850       1860

GluThrSerArgGluAlaProSerIleLeuIleGluPheIleAsnMetPheLeuPhePro
GAGACCTCGAGAGAGGCCCCGAGCATCCTGATCGAGTTCATTAACATGTTCCTGTTCCCA
       1870      1880      1890      1900      1910       1920

ThrSerLysThrHisGlyLeuTyrProGlyGlnAlaHisValGlnArgValLeuValAla
ACCAGCAAGACACACGGGCTCTACCCAGGGCAGGCACACGTCCAGAGAGTGTTGGTGGCT
       1930      1940      1950      1960      1970       1980

LeuThrValLeuAlaValProValLeuPheLeuGlyLysProLeuPheLeuLeuTrpLeu
CTCACGGTGCTGGCTGTCCCCGTGCTCTTCTTAGGAAAGCCGCTTTTTCTGCTGTGGCTG
       1990      2000      2010      2020      2030       2040

HisAsnGlyArgAsnCysPheGlyMetSerArgSerGlyTyrThrLeuValArgLysAsp
CACAACGGGCGCAATTGCTTTGGCATGAGCCGGAGCGGTTACACACTCGTGAGGAAGGAC
       2050      2060      2070      2080      2090       2100

SerGluGluGluValSerLeuLeuGlyAsnGlnAspIleGluGluGlyAsnSerArgMet
AGCGAGGAAGAGGTGTCTCTTCTGGGCAACCAGGACATAGAAGAGGGCAACAGCCGCATG
       2110      2120      2130      2140      2150       2160

GluGluGlyCysArgGluValThrCysGluGluPheAsnPheGlyGluIleLeuMetThr
GAAGAAGGCTGCCGAGAAGTGACGTGTGAGGAGTTTAACTTCGGGGAGATCCTGATGACG
       2170      2180      2190      2200      2210       2220

GlnAlaIleHisSerIleGluTyrCysLeuGlyCysIleSerAsnThrAlaSerTyrLeu
CAGGCCATCCACTCCATTGAGTACTGCCTCGGCTGCATCTCCAACACCGCCTCCTACCTG
       2230      2240      2250      2260      2270       2280

ArgLeuTrpAlaLeuSerLeuAlaHisAlaGlnLeuSerAspValLeuTrpAlaMetLeu
AGGCTCTGGGCACTCAGCCTGGCCCATGCACAGCTCTCTGATGTGCTGTGGGCCATGCTG
       2290      2300      2310       2320      2330      2340

MetArgValGlyLeuArgValAspThrThrTyrGlyValLeuLeuLeuProValMetAla
ATGCGCGTGGGGCTGCGTGTGGACACCACCTATGGGGTCTTGCTGCTGCCTGTCATGGCT
       2350      2360      2370       2380      2390       2400
```

F I G. 1D

PhePheAlaValLeuThrIlePheIleLeuLeuValMetGluGlyLeuSerAlaPheLeu
TTCTTTGCAGTTTTGACCATTTTTATCCTTCTGGTCATGGAGGGTCTTTACGCATTCCTC
    2410      2420      2430      2440      2450      2460

HisAlaIleArgLeuHisTrpValGluPheGlnAsnLysPheTyrValGlyAlaGlyThr
CACGCCATAAGGCTTCACTGGGTAGAATTTCAGAACAAATTCTACGTTGGTGCAGGCACC
    2470      2480      2490      2500      2510      2520

LysPheValProPheSerPheSerLeuLeuSerSerLysPheSerAsnAspAspSerIle
AAGTTTGTTCCCTTCTCCTTCAGTCTGCTCTCCTCCAAGTTCAGTAATGATGACAGCATA
    2530      2540      2550      2560      2570      2580

Ala
GCATGATTGCACGCTGCAGCAAGCCCGCTCTGATCAACGGAGGACTATCATGTTACAGAA
    2590      2600      2610      2620      2630      2640

TTCACTCACTCACTCCGGTCAGAACTTACCAGGGGAAAGTTCCACCCTCGTTGATTGCCT
    2650      2660      2670      2680      2690      2700

TACGATTCAGCCAAATGGTTCTGTAAGATACACCTCTTCCTCATGGTGAAGATTTTGTAA
    2710      2720      2730      2740      2750      2760

AACTCACCACTCCGGACACAGAAATTTCGTTGGTTTTTATTATGAGCAAATATAAGTTAA
    2770      2780      2790      2800      2810      2820

TGCAACGCTACTTTAAAGTTATTTTTTAAAGTGTAAGATTGGAGGAGAGAAGCCAGCTG
    2830      2840      2850      2860      2870

AAGCCAGCTGAACAGCCTAGCTAAAAATGGTCTTAGATACTTGATTCCTTTTCAACTTAA
 2880     2890      2900      2910      2920      2930

AAAAAA
2940

CDNA CLONE FOR T-CELL SUPPRESSOR INDUCER FACTOR

TECHNICAL FIELD

The present invention generally relates to a nucleic acid sequence which encodes for a polypeptide that is at least a part of a T-cell suppressor inducer factor peptide and, in particular, to a cDNA clone for a specific T-cell produced suppressor inducer factor peptide.

BACKGROUND ART

In the immune system, T-cells have at least two major functions; (i) they kill cells that appear foreign, e.g. cells that have been infected with viruses and carry viral antigens; and, (ii) they regulate other immune responses, including B cell antibody production. While the interleukins and a host of lymphokines have been described as effecting positive modulation of the immune response, it has become increasingly evident that the cells responsible for their production are also responsible for the production of other lymphokine-like proteins. Rather than effect positive immune response modulation, these proteins are involved in the "down"0 regulation of the immune system. As a result of their suppression regulating effect, these proteins have been collectively termed T-cell suppressor inducer factor, "TsF1".

Antigen-specific as well as antigen non-specific suppression of the immune response has been demonstrated in a variety of models including leprosy, pregnancy and tumors. However beyond the demonstration of the role and existence for TsF1, the biochemical and molecular genetic proof for the existence of TsF1 has been lacking. No clear consensus has emerged as to the biochemical structure for TsF1. For example, the preliminary biochemistry for each TsF1 varies depending on the reporting laboratory. Mr variances from 19,000 to 90,000 or even larger than 200,000 have been reported. While other T-cell related genes have been cloned and isolated, e.g. U.S. Pat. No. 4,713,332 disclosing a cDNA clone for T-cell antigen receptor, the isolation and cloning of the gene for a TsF1 or any portion thereof has not been reported.

Hence, prior to isolating and cloning of the nucleic acid sequence of the present invention, a need existed for the isolation and molecular characterization for a TsF1 and the gene which encodes for it. By so doing, antibody to TsF1 may be prepared and used to identify cells which produce TsF1 and to perhaps inhibit the down regulatory action of TsF1 on the immune system. Further, such antibody could be used to measure and quantitate TsF1 in vivo. Finally, the characterization of the amino acid sequence for a TsF1 may also be used to produce antibodies which may be used for diagnosis and treatment of human diseases exhibiting a suppressed immune response.

SUMMARY OF THE INVENTION

In accordance with the present invention, a novel putative gene encoding a primate T-cell suppressor inducer factor peptide has been cloned and characterized. In particular, the present invention discloses a putative gene for TsF1 produced by the murine cellular source A.1.1. The present invention also relates to isolation and detailed molecular characterization of A.1.1-produced TsF1 and a method for isolating and screening the T-cell suppressor inducer peptide of both human and murine origin.

One cDNA clone, designated J6B7, containing 2936 base pairs and encoding a protein of 855 amino acids was demonstrated to be a putative gene for A.1.1-produced TsF1. In particular, the following was shown: 1) that the mRNA for clone J6B7 is expressed specifically in T-cells; 2) the clone J6B7 predicts a secretory protein which is comparable in size with the A.1.1-produced TsF1 in size; 3) J6B7 was shown to hybrid select mRNA which can be in vitro translated to a protein which is bound by a TsF1 monoclonal antibody; and, 4) the message encoded by J6B7 was encoded by human and murine T-cells. The foregoing determinants indicate that cDNA clone J6B7 corresponds at least in part to A.1.1-produced TsF1.

Other objects and advantages will be come apparent form the following disclosure of the present invention.

BRIEF DESCRIPTION OF DRAWINGS

FIG. 1A-D is a nucleotide sequence and a deduced amino acid sequence of TsF1 encoded by J6B7 from the initiation codon ATG at position 20 to termination codon TGA at position 2585;

DETAILED DESCRIPTION

It will be appreciated that because of the degeneracy of the genetic code, the nucleotide sequence of the TsF1 gene can vary substantially. For example, portions or all of the gene could be chemically synthesized to yield DNA having a different nucleotide sequence than that shown in FIG. 1, yet the amino acid sequence would be preserved provided that the proper codon-amino acid assignments were observed. Having established TsF1 gene and the amino acid sequence for the protein encoding therefrom, the present invention is not limited to a particular deoxy- or ribo nucleotide sequence, but includes all variations thereof as permitted by-the genetic code.

The cDNA clone of the present invention was obtained by using the murine T-cell hybridoma A.1.1 (University of Alberta, Canada). This cell line functions as the source of TsF1 mRNA used to produce a cDNA library. A.1.1 cells have been shown to produce, constitutively, a soluble peptide, which bind to mAb 14-30, a monoclonal antibody for TsF1. mAb 14-30 has been shown to bind to any TsF1 molecules regardless of antigen specificity or strain of origin of TsF1. The mouse thymoma cell line BW147 (University of Health Sciences/The Chicago Medical School, North Chicago, Ill.) was also used in the present methodology. The methodology and materials of the present invention detailed in the following Examples and disclosed in the drawings, utilize techniques and materials known to an investigator skilled in the art. A discussion of the results of such techniques follows the Examples.

EXAMPLE I

Construction and screening of cDNA library

RNA was isolated from A.1.1 ascites cells by the guanidine isothiocyanate method. The RNA was fractioned on 5-24% sucrose gradient. A portion of each fraction was in vitro translated and the supernatants were tested by Western blot analysis for the reactivity with the polyclonal antisera. As disclosed in FIG. 2A, in vitro translated protein of the mRNA hybrid .-1.selected from A.1.1 (lane 1) and thymus (lane 2) was affinity purified by mAb 14-30. The eluate was separated by SDS-polyacrylamide gel electrophoresis (SDS-PAGE) under reducing conditions and then autoradiographed after treatment of the gel with autoradiography enhances. TsF1 was identified in fractions of mRNA which contain a 3.0–5.0 Kb message. Poly(A)+ RNA from these fractions was used to synthesize cDNA clones.

Figure 2A:
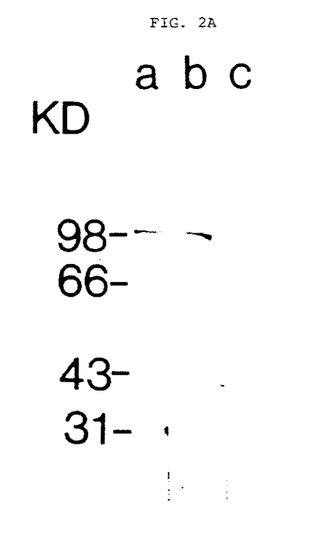
FIG. 2A is Western blot analysis of the in vitro translation products of mRNA selected from A.1.1 and mRNA from thymus.
Figure 2B:
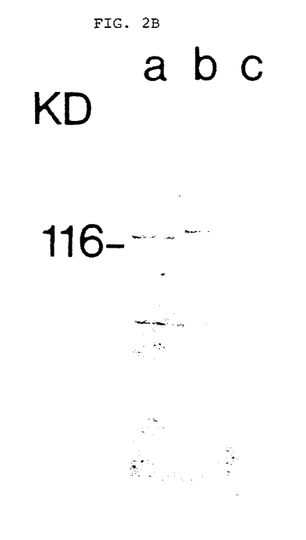
FIG. 2B is Western blot analysis of the fusion peptides produced by gt11 clones.

Double-stranded cDNA was synthesized using a cDNA synthesis system (Pharmacia) and ligated into gt11. About 100,000 recombinant clones contained gt11 expression system and were screened with the polyclonal antibody specific for and alkaline phosphatase-conjugated goat-anti-rabbit immunoglobulin G (Boehringer Mannheim). Two gt11 clones were isolated that directed the synthesis of fusion peptides reactive by Western blot analysis as shown in FIG. 2B. The fusion peptides produced by the gt11 clones were separated on a SDS-PAGE, transferred to nitrocellulose paper and probed with polyclonal antibody and anti-rabbit IgG. As discussed below, of the two clones initially isolated, a 555 bp insert was used to rescreen the library to obtain full length cDNA clones. One clone, designated J6B7, contained a cDNA insert of approximately 3.0 kb and was selected for detailed characterization.

EXAMPLE II

Sequencing of cDNA clones

The gt11 cDNA was subcloned into M13mp19 phages for sequencing. Sequencing was performed by the dideoxy chain-termination method and using the Sequenase ™ enzyme system (USB, Cleveland). A sequential series of overlapping clones was produced by digestion with the 3'---5' exonuclease activity of bacteriophage T4 DNA polymerase using Cyclone I Biosystem ™ (IBI, New Haven, Conn.).

DNA sequences were analyzed with IBI Pustell Sequence Analysis Programs (IBI, New Haven, Conn.), and the EMBO gene bank library #59. Deduced protein sequences were analyzed using the same software and the NBR protein data base.

EXAMPLE III

Hybridization analysis of nucleic acids

Figure 3A:
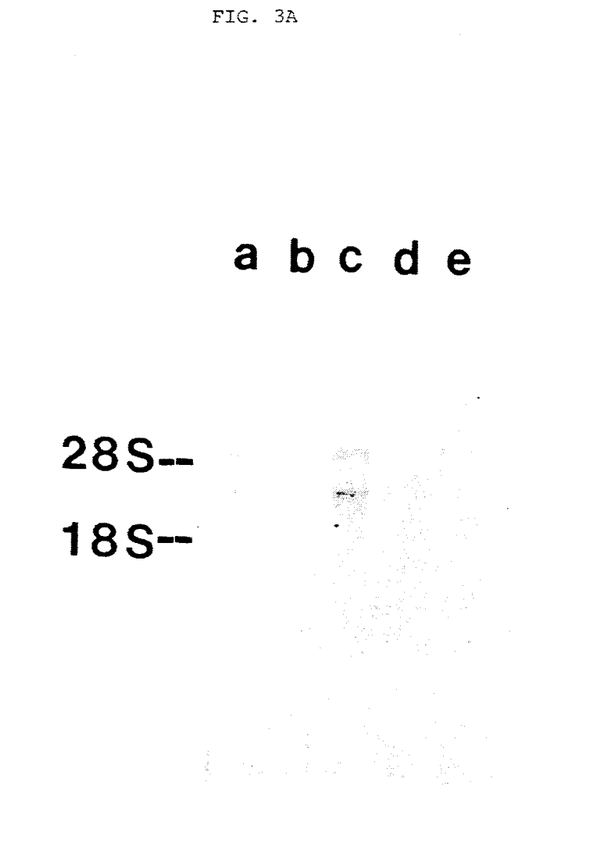
FIG. 3A is Northern blot analysis of five lanes of T and non T-cell RNA hybridized with clone J6B7.
Figure 3B:
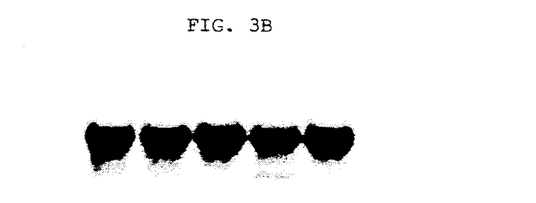
FIG. 3B is the same blot of FIG. 3A reprobed with oligo-labelled 28S rRNA gene; and, FIG. 4 is Southern blot analysis of DNA from B cells, liver cells of BALB/c mouse, and A.1.1 cells.

Northern blot analysis as shown in FIGS. 3A and 3B was used to examine the range of cell types expressing clone J6B7. Ten micrograms of total RNA was electrophoresed on a 1% agarose gel containing 2.2M formaldehyde and blotted onto nitrocellulose paper. Ten micrograms of genomic DNA were digested with the indicated restriction enzymes, electrophoresed on a 0.8% agarose gel, and blotted onto nylon membrane filter (Cuno, Meriden, Conn.).

For both RNA and DNA hybridization experiments, DNA probes were made either by extending the $M^{13}$ universal primer using M13mp19 subclones, or by oligo-labelling (Pharmacia) of the double-stranded cDNA of J6B7, with [$^{32}$P] dCTP (Amersham).

EXAMPLE IV

Immunoblots

SDS-PAGE for Northern, Southern and Western blotting was performed in 8% polyacrylamide gel. Samples were boiled for 5 minutes in a loading buffer containing 1% SDS and 1% 2-mercaptoethanol. The proteins were then electroblotted onto nitrocellulose paper, and allowed to react with the polyclonal antibody and subsequently with an alkaline phosphatase-conjugated anti-rabbit IgG (Boehringer Mannheim).

EXAMPLE V

Hybrid selection and identification of cell-free translation products

Single-stranded M13 DNA containing 3' 1.0 kb of the coding strand of J6B7 was bound to nitrocellulose filters and then hybridized with 2.4mg of total RNA. The mRNA, eluted from the nitrocellulose filter, was translated in a rabbit reticulocyte translation system (Promega) containing $^3$H-leucine. The translated products were tested for the reactivity with mAb 14-30 using mAb 14-30 affinity column or for the biological activity in mixed lymphocyte reaction (MLR). One quarter of the translation product was incubated overnight with mAb 14-30 coupled to Affigel-10 (Biorad), washed with phosphate buffered saline (PBS) and eluted with 20 mM glycine buffer at pH 11.0.

For biological assay, half of each translation produced was diluted to 500 ul with PBS, dialyzed against PBS and subsequently in RPMI-1640 media. For a one way MLR, approximately $1.7 \times 10^5$ cell/well of spleen cells obtained from BALB/c or CBA mouse were used as effector cells and $1.2 \times 10^5$ cells/well of irradiated spleen cells of Swiss/Webster mouse was used as stimulator cells. Cells were cultured in RPMI-1640 media (GIBCO) supplemented with 2-mercaptoethanol ($10^{-5}$M, final concentration)/L-glutamine (2 mM) and 10% fetal calf serum for 4 or 5 days. The in vitro translation products were added in varying concentrations and the proliferation responses were determined by adding 1 uCi of [H$^3$] thymidine per microculture well for (16)hr and harvesting the cultures onto glass fibers. [H$^3$] Thymidine incorporation was measured in a liquid scintillation spectrometer.

EXAMPLE VI

Southern Blot Analysis

A gene coding for antigen-binding molecule of an immunoregulatory protein may be expected to be rearranged to express the diversity of their antigen specificities. To examine this possibility, Southern blot analysis was carried out on two lymphoid cell hybridomas and liver cells using restriction enzymes such as Accl, Hind III and PstI. The results of Southern blot analysis is disclosed in FIG. 4. DNA from B cells (lanes 1, 4 and 7); liver of BALB/c mouse (lanes 2, 5 and 8); and A.1.1 cells (lanes 3, 6 and 9) were digested with Accl (A; lanes 1, 2 and 3); Hind III (H; lanes 4, 5 and 6) and PstI (P; lanes 7, 8 and 9) and then hybridized to oligo-labelled J6B7 cDNA.

RESULTS

From practice of the foregoing methods, the following results were obtained. Approximately 100,000 recombinant clones from an A.1.1 cDNA library contained in the gt11 expression system were screened with the polyclonal antibody specific for TsF1. From this screening, two clones were isolated that directed the synthesis of a TsF1-B-galactosidase fusion peptide reactive with the polyclonal antibody in Western blot. The size of the cDNA of two clones were 555 and 160.bp respectively.

The 555-bp insert cDNA, identified in antibody screening, was used to rescreen the library to obtain full-length TsF1 cDNA clones. The clone J6B7 contained a cDNA insert of approximately 3.0 kb, and due to its size approximation to mRNA for TsF1, was selected for further characterization.

Using Northern blot analysis, a range of cell types expressing J6B7 were examined. FIG. 3A represents one of the Northern autoradiograms obtained by probing with oligo-labelled cDNA of J6B7. To obtain the autoradiogram of FIG. 3A, ten micrograms of total RNA from (1) A.1.1 cells, (2) BW5147 thyoma, (3) thymus of BALB/c mouse, (4) spleen of BALB/c mouse and (5) liver of BALB/c mouse was loaded in each lane. Northern blot analysis proved that TsF1 is expressed specifically in T-cell hybridoma A.1.1 and thymus, and not in thymoma BW5147, spleen or liver. FIG. 3A shows that the size of mRNA identified by the cDNA of J6B7 is approximately 2.9 kb and 5.2 kb in both A.1.1 cells and thymus. The same blot was rehybridized with $^{32}$P-labeled 28S ribosomal RNA gene to show that an equivalent amount of RNA was loaded in each lane as disclosed in FIG. 3B.

The TSF1 produced by A.1.1 cells has been observed to have apparent Mr of 80,000 when analyzed on polyacrylamide gel. Because TsF1 has been shown to have strong tendency to form high molecular weight aggregates, high molecular weight species with Mr of more than 200,000 may be regarded an aggregate of peptides Mr of 80,000.

FIG. 3A disclosed that there may yet be another kind of TsF1 molecule produced by A.1.1 cells, as shown again by the presence of a 5.2 kb mRNA species together with a 2.9 kb mRNA. The mRNA for A.1.1-produced TsF1 is not expressed in thymoma BW5147, although in several instances thymoma BW5147 also appeared to express a protein isotopically related to TsF1. Thymus are shown to express high level of mRNA for TsF1, where the TsF1 expression in spleen is least even though spleen contains substantial amount of T-cells.

Figure 1D:
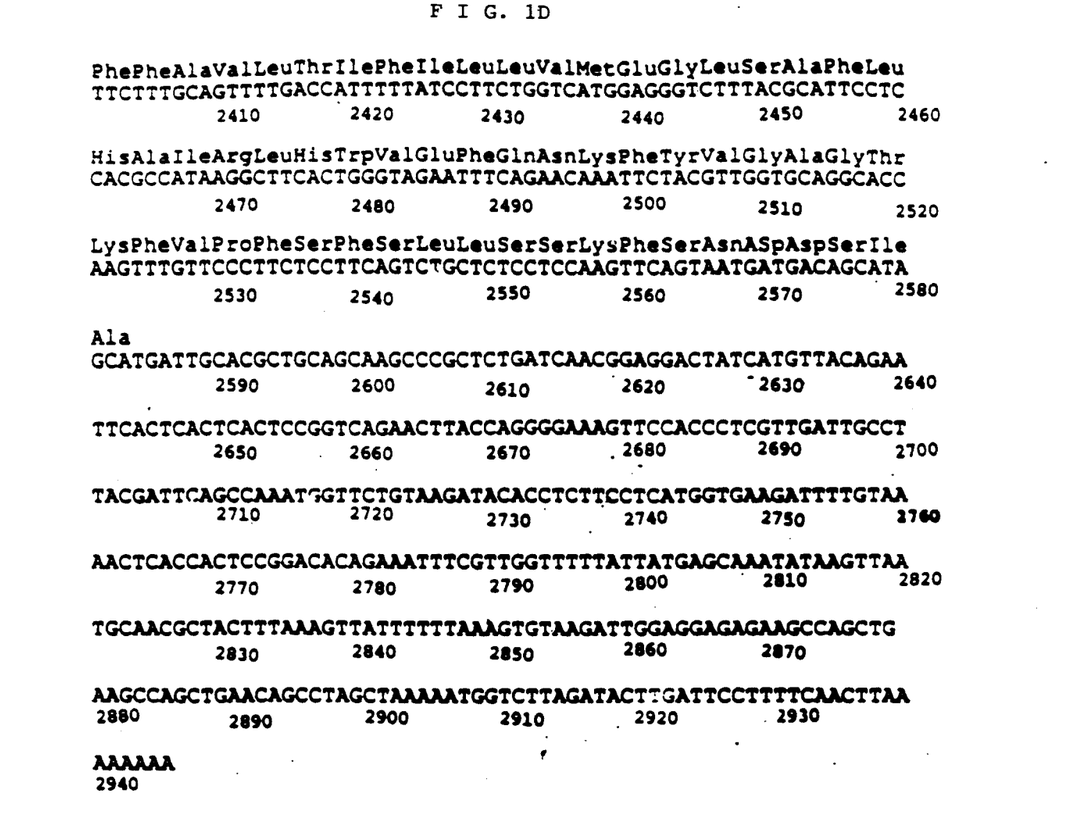

The results of nucleotide sequence analysis and deduced amino acid sequence is disclosed in FIG. 1. The J6B7 clone contains 2936 bp long comprising an encoding sequence of 2565 nucleotides in length encoding a protein of 855 amino acids. The one open reading frame of the encoding sequence begins with an ATG start codon at base number 20 and continuing to a TGA termination site at position 2585. This reading frame utilizes the most 5' ATG, encoding for methionine, which generally is the one utilized in eukaryotic mRNA translation initiation. This encoding predicted a peptide Mr of 98,042 closely corresponding to prior literature Mr predictions of 80,000 for TsF1. Kyte-Doolittle hydrophobicity plot generated from depicted amino acid sequences reveals a very hydrophobic N-terminus of 20 amino acids which is characteristic of a single peptide.

To prove that clone J6B7 encodes for TsF1, hybridization selection and in vitro translation experiments using the J6B7 were performed. As shown in FIG. 2A, the TsF1 mRNA was able to be hybrid selected and in vitro translated to a protein reaction with mAb 14-30 from the RNA isolated from A.1.1 cells and thymus, but not from liver. From the in vitro translated protein of A.1.1 and thymus, two prominent bands of Mr of 98,000 and 115, 000 each and a faint band of Mr of 31,000 were identified as shown in FIG. 2A. Because the cDNA of J6B7 has one open reading frame of Mr 98,042 and the in vitro translated protein shows a prominent band of the same size, it is conceivable that the A.1.1 produced TsF1 with apparent Mr of 80,000 may be the post-transcriptional product of 98,000 dalton peptide. The protein of Mr 115,000 may represent a membrane form of TsF1 peptide which is consistent with prior reports of the existence of a membrane form and soluble form of TsF1. Another possible explanation for these is that the larger species of protein may come from the larger 5.0 kb species mRNA. A protein with Mr of 31,000 appears to be a partial degradation product of a larger molecule.

Figure 4:
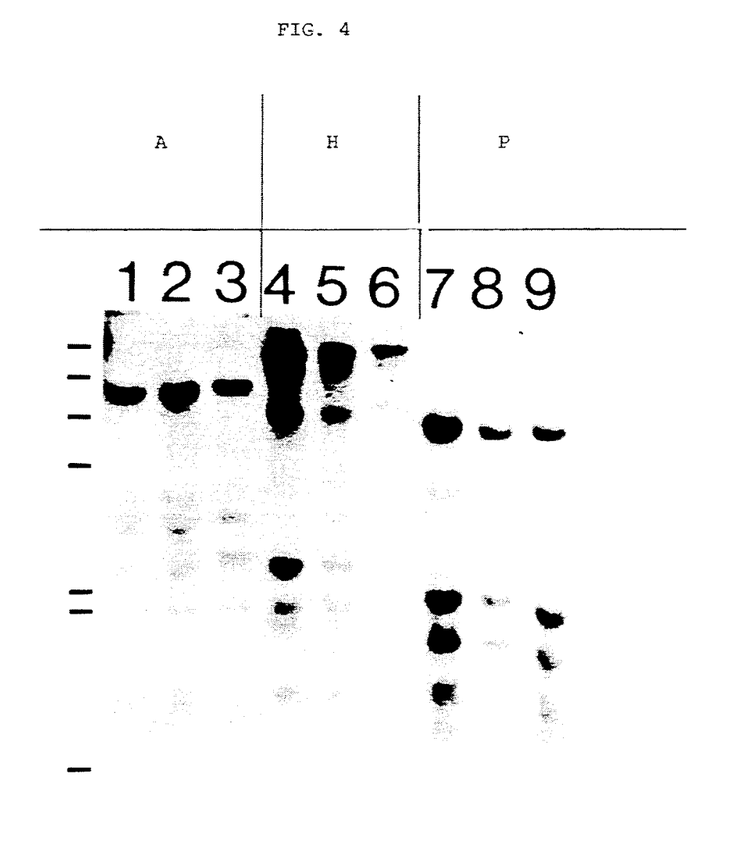

The A.1.1 cells which were used to clone the gene for TsF1 has been characterized for the production of Ag[p18]-specificity. Thus, we examined the possibility of DNA rearrangement by Southern blot analysis, using the full length cDNA of J6B7. FIG. 4, however, reveals no rearrangement of germ-line DNA. Therefore, it is conceivable that the protein encoded by J6B7 may be a molecule with antigen non-specific suppressor function. Production of antigen non-specific suppressor factor as well as antigen specific suppressor factor by the same T-cells has been demonstrated in the regulation of IgE responses. Because another highly related mRNA species of 5.0 kb was identified in both A.1.1 cells and thymus by the cDNA of J6B7, molecular characterizations of this mRNA may provide understanding for the antigen specific T-cell suppressor inducer molecule.

Hence, the present invention generally discloses a nucleic acid sequence containing 2936 base pairs having an encoding sequence 2565 in length and encoding a polypeptide of 690 amino acids which is at least a part of a T-cell suppressor inducer factor, e.g. primate TsF1 and preferably a human TsF1. The present invention more particularly discloses a clone which was demonstrated by the following to be encoding for A.1.1-produced TsF1; (1) the mRNA for the clone is expressed specifically in T-cells; (2) the clone predicts a secretory protein which is comparable in size with the A.1.1-produced TsF1 in size: (3) the clone was shown to hybrid select mRNA which can be in vitro translated to a protein which is bound by monoclonal antibody 14-30; and, (4) the message encoded by the clone was encoded by human and murine T-cells.

The nucleic acid sequences may be used as probes if labeled with a detectable marker, e.g., a radioactive, fluorescent or biotinylated marker. Labeled probe nucleic acid sequences according to the invention may be used, inter alia, to determine whether an unknown cell, such as tumor cell, is a T-cell.

A cDNA sequence according to the invention for insertion into a host may be prepared as follows using techniques known in the art. mRNA is obtained from a cell source producing TsF1 and used to prepare cDNA complementary to the mRNA. The cDNA is inserted into an appropriate cloning vehicle pBR322, which is then inserted into a suitable host, e.g. E. coli. The resulting host is cultured under appropriate conditions permitting production of multiple copies of the cDNA, and the cDNA so produced is recovered and screened to determine whether it is expressed only in T-cells.

Host cells containing a suitable cloning vehicle which includes cDNA encoding the T-cell antigen receptor may be prepared and used to produce the receptor polypeptide in accordance with methods known to those of ordinary skill in the art.

Antibodies to the polypeptides, e.g., monoclonal or serum-derived antibodies, may be prepared using methods known to those skilled in the art. Such antibodies may be employed to detect the presence of T-cell receptor antigen and to determine whether an unknown cell, e.g., a tumor cell, is a T-cell. To do so, the sample to be tested is treated with the antibody under suitable conditions permitting formation of antigen antibody complex and a determination made whether complex is present.

In summary, J6B7 contains unique coding sequences which are not rearranged. This mRNA is highly expressed by some T-cells. The mRNA that hybrid selected by J6B7 can be translated in vitro to a protein that can be recognized by mAb 14-30 as well as two polyclonal antibodies which have been characterized for the reactivity with T-cell produced proteins involved in the down regulation of the immune response. The peptide obtained by hybrid selection and translation in vitro shows non-specific suppressive activity in a one way MLR. Therefore, all of these observations suggest that J6B7 contains a cDNA coding for an antigen non-specific T-cell suppressor factor.

While the specific embodiments have been illustrated and described, numerous modifications come to mind without significantly departing from the spirit of the invention and the scope of protection is only limited by the scope of the accompanying claims.

I claim:

1. A nucleic acid sequence encoding a polypeptide consisting of a T-cell suppressor inducer factor.
2. The nucleic acid of claim 1 wherein the nucleic acid sequence comprises 2936 nucleotides.
3. The nucleic acid of claim 2 further including a polypeptide encoding sequence being 2565 nucleotides in length.
4. The nucleic acid of claim 3 wherein the polypeptide encoding sequence encodes for 690 amino acids of the T-cell suppressor inducer factor.
5. The nucleic acid of claim 4 wherein the polypeptide is about 98,000 Daltons.
6. The nucleic acid of claim 1 wherein the nucleic acid is DNA.
7. The nucleic acid of claim 6 wherein the nucleic acid is cDNA.
8. The nucleic acid of claim 1 wherein the nucleic acid is RNA.
9. A recombinant nucleic acid sequence which encodes the polypeptide T-cell suppressor inducer factor, the amino acid sequence comprising:

MetGlySerLeuPheArgSerGluSerMetCysLeuAlaGln

LeuPheLeuGlnSerGlyThrAlaTyrGluCysLeuSerAlaLeuGlyGluLysGlyLeu

ValGlnPheArgAspLeuAsnGlnAsnValSerSerPheGlnArgLysPheValGlyGlu

ValLysArgCysGluGluLeuGluArgIleLeuValTyrLeuValGlnGluIleThrArg

AlaAspIleProLeuProGluGlyGluAlaSerProProAlaProProLeuLysHisVal

LeuGluMetGlnGluGlnLeuGlnLysLeuGluValGluLeuArgGluValThrLysAsn

LysGluLysLeuArgLysAsnLeuLeuGluLeuValGluTyrThrHisMetLeuArgVal

ThrLysThrPheLeuLysArgAsnValGluPheGluProThrTyrGluGluPheProAla

LeuGluAsnAspSerLeuLeuAspTyrSerCysMetGlnArgLeuGlyAlaLysLeuGly

PheValSerGlyLeuIleGlnGlnGlyArgValGluAlaPheGluArgMetLeuTrpArg

AlaCysLysGlyTyrThrIleValThrTyrAlaGluLeuAspGluCysLeuGluAspPro

GluThrGlyGluValIleLysTrpTyrValPheLeuIleSerPheTrpGlyGluGlnIle

GlyHisLysValLYsLysIleCysASpCysTyrHisCysHisIleTyrProTyrProAsn

ThrAlaGluGluARgARgGluIleGlnGluGlyLeuAsnThrArgIleGlnASpLeuTyr

ThrValLeuHisLysThrGluAspTyrLeuArgGlnValLeuCysLysAlaAlaGluSer

ValCysSerArgValValGlnValArgLysMetLysAlaIleTyrHisMetLeuAsnMet

CysSerPheAspValThrAsnLYsCysLeuIleAlaGluValTrpCysProGluValAsp

LeuProGlyLeuArgArgAlaLeuGluGluGlySerArgGluSerGlyAlaThrIlePro

SerPheMetASnThrIleProThrLysGluThrProProThrLeuIleArgThrAsnLys

PheThrGluGlyPheGlnAsnIleValAspAlaTyrGlyValGlySerTyrARgGluVal

AsnProAlaLeuPheThrIleIleThrPheProPheLeuPheAlaValMetPheGlyAsp

PheGlyHisGlyPheValMetPheLeuPheAlaLeuLeuLeuValLeuAsnGluAsnHis

ProArgLeuSerGlnSerGlnGluIleLeuARgMetPhePheAspGlyArgTyrIleLeu

LeuLeuMetGlyLeuPheSerValTyrThrGlyLeuIleTyrAsnAspCysPheSerLys

SerValAsnLeuPheGlySerGlyTrpAsnValCysAlaMetTyrSerSerSerHisSer

ProGluGluGlnArgLysMetValLeuTrpAsnAspSerThrIleArgHisSerArgThr

LeuGlnLeuAspProAsnIleProGlyValPheArgGlyProTyrProPheGlyIleAsp

ProIleTrpAsnLeuAlaThrAsnArgLeuThrPheLeuASnSerPheLysMetLysMet

SerValIleLeuGlyIlePheHisMetThrPheGlyValValLeuGlyIlePheAsnHis

LeuHisPheArgLysLysPheAsnValTyrLeuValSerValProGluIleLeuPheMet

LeuCysIlePheGlyTyrLeuIlePheMetIleIleTyrLysTrpLeuAlaTyrSerAla

GluThrSerArgGluAlaProSerIleLeuIleGluPheIleAsnMetPheLeuPhePro

ThrSerLysThrHisGlyLeuTyrProGlyGlnAlaHisValGlnArgValLeuValAla

LeuThrValLeuAlaValProValLeuPheLeuGlyLysProLeuPheLeuLeuTrpLeu

HisAsnGlyArgASnCysPheGlyMetSerARgSerGlyTyrThrLeuValArgLysAsp

SerGluGluGluValSerLeuLeuGlyAsnGlnASpIleGluGluGlyAsnSerArgMet

GluGluGlyCysArgGluValThrCysGluGluPheAsnPheGlyGluIleLeuMetThr

GlnAlaIleHisSerIleGluTyrCysLeuGlyCysIleSerAsnThrAlaSerTyrLeu

ArgLeuTrpAlaLeuSerLeuAlaHisAlaGlnLeuSerAspValLeuTrpAlaMetLeu

MetArgValGlyLeuArgValASpThrThrTyrGlyValLeuLeuLeuProValMetAla

PhePheAlaValLeuThrIlePheIleLeuLeuValMetGluGlyLeuSerAlaPheLeu

HisAlaIleArgLeuHisTrpValGluPheGlnAsnLysPheTyrValGlyAlaGlyThr

LysPheValProPheSerPheSerLeuLeuSerSerLysPheSerAsnASpAspSerIle

Ala.

10. A recombinant nucleic acid sequence which encodes the polypeptide T-cell suppressor inducer factor, the nucleotide sequence comprising:

ATGGGCTCTCTCTTCCGCAGCGAGAGCATGTGCCTGGCGCAG

CTCTTCCTGCAGTCGGGCACGGCCTACGAGTGTCTGAGCGCGCTGGGCGAGAAGGGCCTG

GTGCAGTTCCGAGACCTCAATCAAAATGTAAGTTCTTTTCAAAGAAAATTCGTCGGTGAG

GTAAAGAGGTGTGAAGAGCTCGAACGAATACTGGTGTACCTGGTGCAGGAAATCACCAGA

GCTGATATTCCCCTGCCTGAAGGAGAGGCCAGTCCTCCCGCACCACCTCTTAAACATGTC

CTAGAAATGCAGGAACAGCTGCAGAAGCTGGAGGTGGAGCTCAGAGAAGTCACCAAGAAC

AAGGAGAAGCTGAGGAAGAACCTGTTGGAGCTGGTGGAGTACACCCACATGCTGAGGGTC

ACGAAGACCTTCCTCAAGCGGAATGTGGAGTTTGAGCCCACGTATGAAGAGTTTCCCGCC

TTAGAGAACGACTCTCTGTTGGACTACAGCTGCATGCAGCGGCTGGGCGCCAAGCTGGGA

TTCGTTTCTGGCCTGATTCAGCAAGGCAGAGTTGAAGCATTTGAAAGGATGCTGTGGCGG

GCCTGCAAAGGGTACACCATTGTGACCTATGCAGAGCTGGACGAGTGCCTGGAGGACCCT

GAAACGGGTGAAGTCATAAAGTGGTACGTGTTCCTGATTTCCTTTTGGGGAGAGCAGATT

GGCCACAAGGTTAAGAAGATATGTGACTGTTACCACTGCCACATCTACCCGTATCCAAAC

ACGGCTGAGGAGCGCAGGGAGATTCAGGAGGGGCTCAATACTCGGATCCAAGACCTTTAC

ACGGTGCTGCACAAAACGGAGGACTATCTGCGGCAAGTGCTCTGCAAAGCTGCCGAGTCC

GTGTGCAGCCGTGTGGTCCAGGTGAGGAAGATGAAGGCCATCTACCACATGCTCAACATG

TGCAGCTTTGACGTCACCAACAAGTGCCTCATAGCTGAGGTCTGGTGCCCCGAGGTGGAC

CTGCCAGGCTTGCGCAGAGCACTGGAGGAAGGCTCGAGAGAGAGCGGAGCTACAATCCCC

-continued

```
TCGTTCATGAACACAATCCCTACGAAAGAAACACCCCCCACTCTGATCCGCACCAACAAA
TTCACTGAAGGTTTCCAGAACATCGTGGATGCCTATGGAGTCGGGAGCTACAGAGAAGTG
AACCCAGCTCTCTTTACCATCATCACCTTCCCGTTCCTGTTTGCTGTGATGTTTGGCGAC
TTTGGGCACGGCTTTGTCATGTTCCTGTTTGCCCTCTTACTGGTGTTAAATGAGAATCAC
CCCAGACTAAGCCAGTCACAGGAGATCCTTAGGATGTTCTTTGACGGCCGGTATATCCTG
CTGCTGATGGGGCTGTTCTCTGTGTACACCGGCCTCATCTACAACGACTGCAAGAGGTTC
TCTGTGAACCTCTTTGGTTCTGGGTGGAACGTATGTGCCATGTACAGCTCCAGCCACTCT
CCAGAGGAGCAGAGGAAGATGGTACTTTGGAATGACAGCACCATCAGGCACAGCAGAACT
TTGCAGCTGGACCCGAATATCCCTGGAGTTTTCCGAGGCCCCTACCCTTTTGGCATTGAT
CCTATTTGGAACCTGGCCACAAACCGCCTCACGTTCCTCAACTCCTTCAAGATGAAAATG
TCTGTGATTTTAGGAATTTTTCACATGACTTTTGGTGTTGTTCTGGGAATATTTAACCAC
TTGCACTTTAGGAAGAAGTTCAACGTCTACCTGGTCTCGGTGCCTGAGATCCTGTTCATG
CTCTGCATCTTTGGGTACCTGATTTTCATGATCATTTACAAGTGGCTGGCATACTCGGCA
GAGACCTCGAGAGAGGCCCCGAGCATCCTGATCGAGTTCATTAACATGTTCCTGTTCCCA
ACCAGCAAGACACACGGGCTCTACCCAGGGCAGGCACACGTCCAGAGAGTGTTGGTGGCT
CTCACGGTGCTGGCTGTCCCCGTGCTCTTCTTAGGAAAGCCGCTTTTTCTGCTGTGGCTG
CACAACGGGCGCAATTGCTTTGGCATGAGCCGGAGCGGTTACACACTCGTGAGGAAGGAC
AGCGAGGAAGAGGTGTCTCTTCTGGGCAACCAGGACATAGAAGAGGGCAACAGCCGCATG
GAAGAAGGCTGCCGAGAAGTGACGTGTGAGGAGTTTAACTTCGGGGAGATCCTGATGACG
CAGGCCATCCACTCCATTGAGTACTGCCTCGGCTGCATCTCCAACACCGCCTCCTACCTG
AGGCTCTGGGCACTCAGCCTGGCCCATGCACAGCTCTCTGATGTGCTGTGGGCCATGCTG
ATGCGCGTGGGGCTGCGTGTGGACACCACCTATGGGGTCTTGCTGCTGCCTGTCATGGCT
TTCTTTGCAGTTTTGACCATTTTTATCCTTCTGGTCATGGAGGGTCTTTACGCATTCCTC
CACGCCATAAGGCTTCACTGGGTAGAATTTCAGAACAAATTCTACGTTGGTGCAGGCACC
AAGTTTGTTCCCTTCTCCTTCAGTCTGCTCTCCTCCAAGTTCAGTAATGATGACAGCATA
GCATGA.
```

UNITED STATES PATENT AND TRADEMARK OFFICE
CERTIFICATE OF CORRECTION

PATENT NO. : 5,196,526

DATED : March 23, 1993

INVENTOR(S) : Kenneth D. Beaman

It is certified that error appears in the above-identified patent and that said Letters Patent is hereby corrected as shown below:

Column 1, line 25, delete "O".

Column 2, line 46, after "established" insert therefor --the nucleotide sequence for A.1.1-produced--.

Column 5, line 36, replace "TSF1" with --TsF1--.

Column 6, line 42, replace "690" with --855--.

In the Claims:

Claim 4, Column 8, line 17, replace "690" with --855--.

Signed and Sealed this

Eighteenth Day of January, 1994

Attest:

BRUCE LEHMAN

Attesting Officer

Commissioner of Patents and Trademarks